United States Patent
Mirza

(10) Patent No.: US 12,014,824 B1
(45) Date of Patent: Jun. 18, 2024

(54) INTERACTIVE HEALTH CARE SYSTEM FOR MANAGING BACK OR NECK PAIN

(71) Applicant: PEER Technologies PLLC, Fairfax, VA (US)

(72) Inventor: Sohail K. Mirza, Fairfax, VA (US)

(73) Assignee: PEER Technologies PLLC, Fairfax, VA (US)

( * ) Notice: Subject to any disclaimer, the term of this patent is extended or adjusted under 35 U.S.C. 154(b) by 0 days.

(21) Appl. No.: 16/562,385

(22) Filed: Sep. 5, 2019

Related U.S. Application Data

(60) Provisional application No. 62/727,432, filed on Sep. 5, 2018.

(51) Int. Cl.
*G16H 50/20* (2018.01)
*A61B 5/00* (2006.01)
(Continued)

(52) U.S. Cl.
CPC ......... *G16H 50/20* (2018.01); *A61B 5/02055* (2013.01); *A61B 5/1121* (2013.01); *A61B 5/14532* (2013.01); *A61B 5/14542* (2013.01); *A61B 5/4809* (2013.01); *A61B 5/4824* (2013.01); *A61B 5/7435* (2013.01); *G16H 10/20* (2018.01); *G16H 10/60* (2018.01); *G16H 15/00* (2018.01); *G16H 40/67* (2018.01); *G16H 50/30* (2018.01); *G16H 50/70* (2018.01); *G16H 70/60* (2018.01); *A61B 5/024* (2013.01)

(58) Field of Classification Search
CPC ........ G16H 50/20; G16H 50/70; G16H 10/20; G16H 10/60; G16H 15/00; G16H 70/60; G16H 40/67; G16H 50/30; A61B 5/4824; A61B 5/7435; A61B 5/02055; A61B 5/4809; A61B 5/1121; A61B 5/024
See application file for complete search history.

(56) References Cited

U.S. PATENT DOCUMENTS

| | | | |
|---|---|---|---|
| 2016/0198996 A1* | 7/2016 | Dullen | A61B 5/6832 600/301 |
| 2016/0220179 A1* | 8/2016 | Rigoard | A61B 5/4824 |

(Continued)

FOREIGN PATENT DOCUMENTS

| | | | | |
|---|---|---|---|---|
| GB | 2404864 A | * | 2/2005 | A61H 23/02 |

OTHER PUBLICATIONS

Jibb, User-Centered Design Approach to the Development and Pilot Testing of a Smartphone App To Support Real-Time Pain Management for Adolescents with Cancer, 2017, ProQuest LLC, pp. 1-269 (Year: 217).*

*Primary Examiner* — Christopher L Gilligan
(74) *Attorney, Agent, or Firm* — Loginov & Associates, PLLC; William A. Loginov

(57) ABSTRACT

An interactive guide that guides a user (e.g., a patient, family member, caregiver, or anyone else with the permission of the patient) from an initial diagnosis (e.g., back pain), prognosis, surgery (if elected), rehabilitation, to long-term care after treatment. The guide can provide personalized guidance and information to the user based on information provided by the user, either through surveys or one or more sensors, to provide personalized predictive information to the user. The guide also allows a collaborative effort between the patient and the caregiver to make the best decisions regarding treatment for the patient.

5 Claims, 10 Drawing Sheets

(51) Int. Cl.
<table>
<tr><td>A61B 5/0205</td><td>(2006.01)</td></tr>
<tr><td>A61B 5/024</td><td>(2006.01)</td></tr>
<tr><td>A61B 5/11</td><td>(2006.01)</td></tr>
<tr><td>A61B 5/145</td><td>(2006.01)</td></tr>
<tr><td>G16H 10/20</td><td>(2018.01)</td></tr>
<tr><td>G16H 10/60</td><td>(2018.01)</td></tr>
<tr><td>G16H 15/00</td><td>(2018.01)</td></tr>
<tr><td>G16H 40/67</td><td>(2018.01)</td></tr>
<tr><td>G16H 50/30</td><td>(2018.01)</td></tr>
<tr><td>G16H 50/70</td><td>(2018.01)</td></tr>
<tr><td>G16H 70/60</td><td>(2018.01)</td></tr>
</table>

(56) References Cited

U.S. PATENT DOCUMENTS

| | | | |
|---|---|---|---|
| 2017/0173262 A1* | 6/2017 | Veltz | G16H 20/17 |
| 2018/0015284 A1* | 1/2018 | Coleman | G16H 40/63 |
| 2018/0193652 A1* | 7/2018 | Srivastava | A61B 5/4848 |
| 2019/0175100 A1* | 6/2019 | Etleb | G01L 1/205 |
| 2019/0313966 A1* | 10/2019 | Lanzkowsky | G06K 9/00302 |
| 2019/0362843 A1* | 11/2019 | Lin | G16H 40/63 |

\* cited by examiner

Return Back and Neck Pain

Feb 22, 2018
Xxxxx Xxxxx
Born: Xxx XX, XXXX
Patient ID: 1234567
Encounter ID: 111
Age: 73 years
Gender: Female

Section 1 - Pain Intensity

☑ I have no pain at the moment.

○ The pain is very mild at the moment,

○ The pain is moderate at the moment.

○ The pain is fairly severe at the moment.

○ The pain is very severe at the moment.

○ The pain is the worst imaginable at the moment,

Section 2- Personal Care (washing, dressing, etc.)

☑ I can look after myself normally without causing extra pain,

○ I can look after myself normally but it causes extra pain,

○ It is painful to look after myself and I am slow and careful.

○ I need some help but manage most of my personal care,

○ I need help every day in most aspects of self-care.

○ I do not get dressed; I wash with difficulty and stay in bed

Section 3- Lifting

○ I can lift heavy weights without extra pain.

○ I can lift heavy weights but it gives extra pain.

PEER_1234567_20180222_Xxxxx_Xxxx PRÓ_111.pdf

FIG. 4

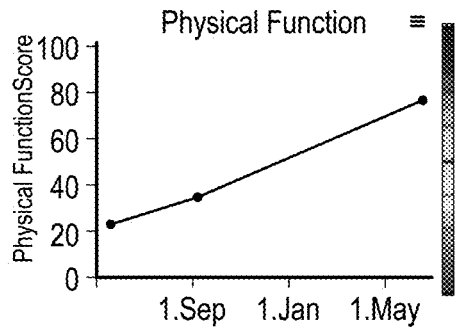

Physical Function (last updated 03/11/2018)

The average score is 50.
Your score is 43 (range 40 to 46)
Your score is higher (better) than:
- 31 percent of people in the general population
- 34 percent of people age 45-54
- 35 percent of females

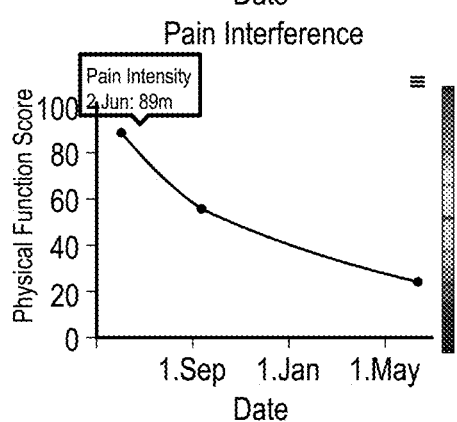

Pain Interference (last updated 03/11/2018)

The average score is 50.
Your score is 69 (range 67 to 71)
Your score is higher (worse) than:
- 96 percent of people in the general population
- 93 percent of people age 45-54
- 95 percent of females

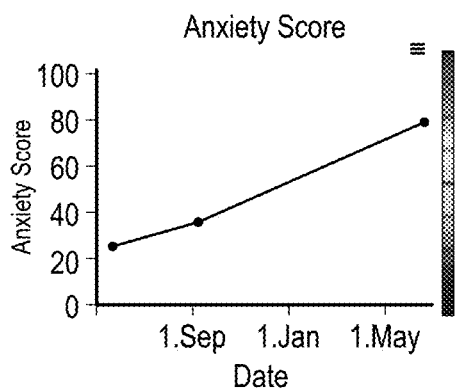

Anxiety (last updated 03/11/2018)

The average score is 50
Your score is 42 (range 40 to 46)
Your score is lower (better) than:
- 78 percent of people in the general population
- 89 percent of people age 45-54
- 87 percent of females

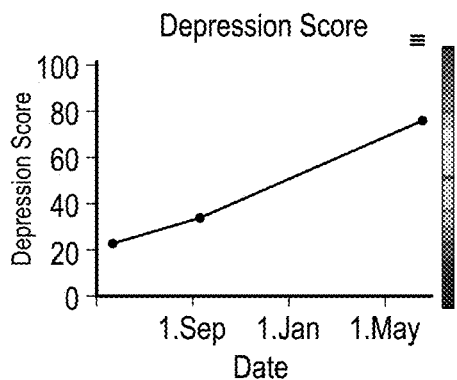

Depression (last updated 03/11/2018)

The average score is 50.
Your score is 76 (range 74 to 78)
Your score is higher (worse) than:
- 67 percent of people in the general population
- 74 percent of people age 45-54
- 80 percent of females

FIG. 5

Summary of Neck Pain History (last updated 11/23/2017)
Duration: More than 5 years
Frequency: Every day or nearly every day in the past 6 months
Pain in arm: Yes, only on the left side
Numbness in hands: Yes, both sides
Ever had neck surgery: Yes, more than one operation
Time since neck surgery: Less than 6 months
Type of neck surgery: No fusion
Ever had neck injection: Yes, more than one injection
Time since last neck injection: Yes, more than one injection

Social History (last updated 11/23/2017)
Height: 5ft 11 in
Weight: 138.0
BMI: 19.24
Smoking Status: Never smoked
Alcohol used more than you meant: Sometimes
Alcohol wanted to cut down: Never
Employment Status: Sick leave or maternity leave
Education Level: No high school diploma
Race: Black or African-American
Ethnicity: Not Hispanic or Latino

General History (last updated 11/23/2017)
Ever had physical therapy: Yes
Time since last physical therapy session: Less than 6 months ago
Ever used opioid pain killers: Yes
Currently taking opioids: Yes
Cognitive behavioral therapy: Yes
Time off work: Yes, more than 1 month
Applied for disability: Yes, workers compensation
Involved in a lawsuit: No
Symptoms related to: Not employment, auto accident, other accident, or pregnancy
Stomach pain: Not bothered at all
Headaches: Not bothered at all
Pain in arms or legs: Not bothered at all
Widespread pain: Not bothered at all
Beliefs: Agree, it's not safe to be physically active
        Agree, pain is never going to get better
Beliefs: Reduce pain enough so I can function

Comorbidity (last updated 11/23/2017)
1. Asthma (145)
2. Emphysema (343.00XA)
3. Peptic Ulcer (164.01)
4. Pain in limb (M79 6)
5. Pain in back (M54.1)
No Chronic Ischemic Heart Disease, Heart Failure, Peripheral Arterial Disease. Cerebral Infarction. Type2 Diabetes Mellitus, Chronic Kidney Disease, Rheumatoid Arthritis with Rheumatoid Factor, Alzheimer's Disease. Fibrosis and cirrhosis of liver, History of malignant neoplasm, unspecified, HIV Disease

FIG.6

INTERACTIVE HEALTH CARE SYSTEM FOR MANAGING BACK OR NECK PAIN

RELATED APPLICATIONS

This application claims the benefit of U.S. Provisional Application Ser. No. 62/727,432, filed Sep. 5, 2018, entitled INTERACTIVE HEALTH CARE SYSTEM FOR MANAGING BACK OR NECK PAIN, the entire disclosure of which is herein incorporated by reference.

This application is also related to U.S. patent application Ser. No. 15/470,819, filed Mar. 27, 2017, entitled SYSTEM AND METHODS FOR INTERACTIVE HEALTH CARE, and U.S. Provisional Application Ser. No. 62/313,548, filed Mar. 25, 2016, entitled SYSTEM AND METHODS FOR INTERACTIVE HEALTH CARE, the entire disclosures of each of which are herein incorporated by reference.

FIELD OF THE INVENTION

The present disclosure relates to an interactive health care guide that guides a user from an initial diagnosis, prognosis, surgery, rehabilitation, to long-term care after treatment.

BACKGROUND OF THE INVENTION

In a traditional clinical setting, a health care professional provides health care services when a patient visits during an appointment. During the appointment, the flow of information between patient and professional may be incomplete in the sense that the patient forgets certain details regarding pain, physical ability, or mental function. In some instances, a patient may even withhold certain information out of fear of embarrassment or discomfort discussing certain subjects. In other instances, a patient may have questions that arise after the appointment. Typically, the patient must call the health care professional or schedule another appointment to address such questions.

One alternative is for the patient to browse the internet, such as WebMD or other medical websites. However, such websites often don't provide the most accurate information and are not personalized to the particular patient. Further, such websites can provide potential diagnoses that do not apply to the patient, causing the unfounded escalation of concerns about common symptomology based on review of search results and literature online. This is known as "cyberchondria" and can cause unnecessary stress in anxiety in patients.

Chronic back pain (cLBP) is a major and growing source of pain and disability. In U.S. national surveys, LBP is the most frequent type of pain, reported by about half of adults in the past year. It accounts for 34 million office visits annually to primary care physicians (PCP). cLBP most commonly occurs without radicular symptoms and cannot be reliably attributed to a specific cause ("non-specific cLBP"). The optimal strategy for treating such patients is uncertain. The efficacy of treatments is moderate at best and a significant proportion develop persistent disabling cLBP despite use of first-line therapies such as analgesics, exercise therapy, or cognitive behavioral therapy (CBT). Invasive treatments and surgery have limited efficacy and significant risks. An estimated 7 million adults have activity limitations due to cLBP.30 It is considered one of the most vexing health problems of our time. The Institute of Medicine included "Comparing the effectiveness of treatment strategies for low back pain without neurological deficit or spinal deformity" in the top quartile of 100 research priorities in 2009.

SUMMARY OF THE INVENTION

The present disclosures provides interactive technology to help patients with personalized Shared Decision Making (SDM) on appropriateness of the wide range of treatments available for cLBP. Too frequently patients are unable to match their treatment decisions with their preferences because they do not fully understand the risks and benefits of the different options. Patients frequently hold mistaken beliefs about their diagnosis and risks/benefits associated with treatments. The present technology will help align an individual patient's values and preferences with the patient's treatment choice through SDM and provides a technological solution to the problem of cyberchondria.

The present disclosure provides an interactive guide that guides a user (e.g., a patient, family member, caregiver, or anyone else with the permission of the patient) from an initial diagnosis (e.g., back pain), prognosis, surgery (if elected), rehabilitation, to long-term care after treatment. The guide can provide personalized guidance and information to the user based on information provided by the user, either through surveys or one or more sensors, to provide personalized predictive information to the user. The guide also allows a collaborative effort between the patient and the caregiver to make the best decisions regarding treatment for the patient.

The present disclosure also endeavors to incentivize, motivate patients to complete Patient Reported Outcomes (PRO) easily and quickly on their own (pause, resume, automated reminders; help patients understand what their scores and trends mean in the context of their situation; and motivate patients to share their PRO reports with their care team and use their scores during treatment discussions and care plan decisions.

BRIEF DESCRIPTION OF THE DRAWINGS

The invention description below refers to the accompanying drawings, of which:

FIG. 4 depicts examples questions answered by a patient during one or more PRO measures;

FIG. 5 depicts charts depicting a portion of a structured report including benchmarks for physical function, pain interference, anxiety, and depression;

FIG. 6 depicts a portion of a structured report including patient history; and

DETAILED DESCRIPTION

The present disclosure provides an interactive guide that guides a user (e.g., a patient, family member, caregiver, or anyone else with the permission of the patient) from an initial diagnosis (e.g., back pain), prognosis, surgery (if elected), rehabilitation, to long-term care after treatment. The guide can provide personalized guidance and information to the user based on information provided by the user, either through surveys or one or more sensors, to provide personalized predictive information to the user. The guide also allows a collaborative effort between the patient and the caregiver to make the best decisions regarding treatment for the patient.

The present disclosure also endeavors to incentivize, motivate patients to complete Patient Reported Outcomes (PRO) easily and quickly on their own (pause, resume, automated reminders; help patients understand what their scores and trends mean in the context of their situation; and motivate patients to share their PRO reports with their care team and use their scores during treatment discussions and care plan decisions.

Figure 1:
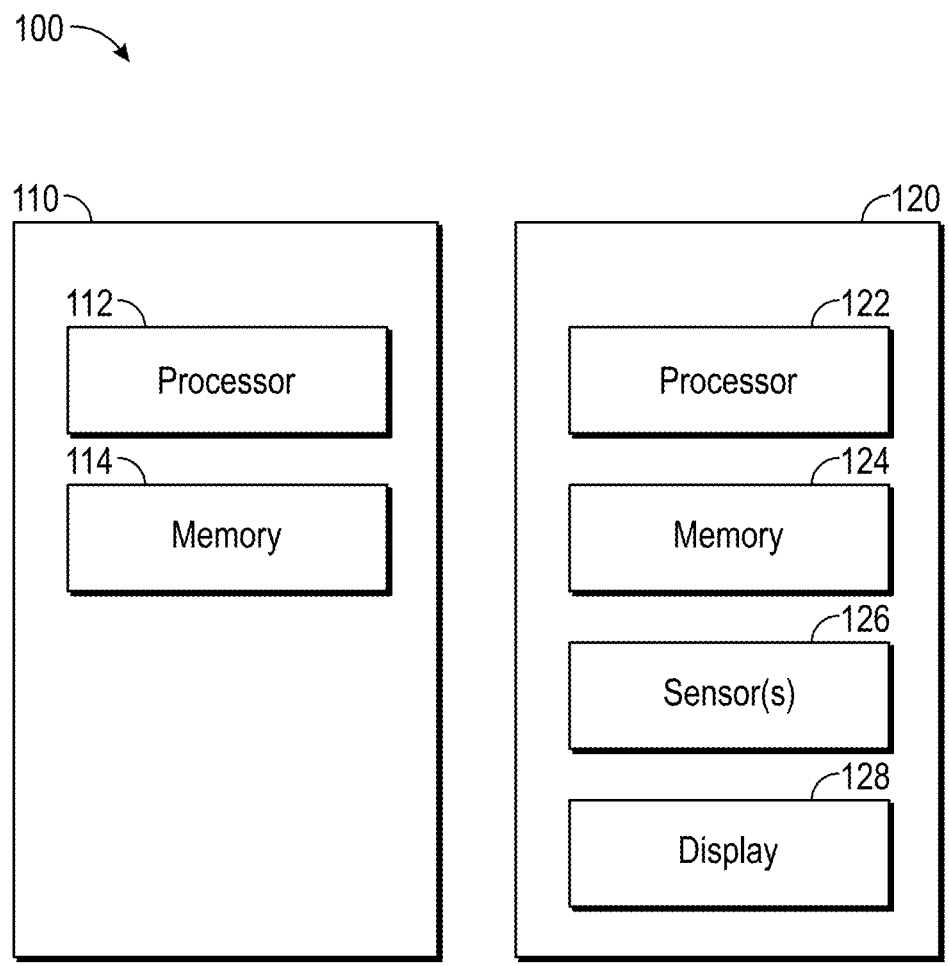
FIG. 1 is an overview of a system for interactive health care according to one or more aspects of the disclosure.

FIG. 1 is an overview of a system for interactive health care according to one or more aspects of the disclosure. As shown, the system 100 may include a computer 110 and a client device 120.

The computer 110 may include a processor 112, a memory 114, and any other components typically present in general purpose computers. The memory 114 may store information accessible by the processor 112, such as instructions that may be executed by the processor or data that may be retrieved, manipulated, or stored by the processor. Although FIG. 1 illustrates processor 112 and memory 114 as being within the same block, it is understood that the processor 112 and memory 114 may respectively comprise one or more processors and/or memories that may or may not be stored in the same physical housing. In one example, computer 110 may be a server that communicates with one or more client devices 120, directly, indirectly, wired, or wirelessly, or via one or more networks (not shown).

The client device 120 may be configured similarly to the computer 110, such that it may include processor 122, a memory 124, and any other components typically present in a general purpose computer. The client device 120 may be any type of computing device, such as a personal computer, tablet, mobile phone, laptop, PDA, wearable fitness device (e.g., FitBit®, Apple® Watch, etc.), etc.

The client device 120 may also include one or more sensors 126. The one or more sensors may be formed integrally with the client device 120, such as within a housing of the client device 120 or semi-permanently or permanently attached to the device 120, or may be removably attached to the client device 120, such as via one or more data and/or power ports disposed on the device (e.g., USB, microUSB, Lightning®, etc.). In another example, the one or more sensors can be a stand-alone sensor and may not be coupled with a processor and/or memory.

In one example, the one or more sensors can include a touch screen sensor capable of accepting user input by one finger (tap, double tap, tap and hold, flick, drag) and two-finger (tap, double tap, tap and hold, pinch out, pinch in, rotate, flick, drag) gestures on the device touch screen to navigate the interactive guide contents and activate functions.

The one or more sensors can also include one or more accelerometers and/or gyroscopes. Such sensors can be used to track activity and movement such as knee range of motion and device orientation for modifying display and contents.

The one or more sensors can also include one or more Global Positioning System (GPS) sensors. GPS sensors in the device are used identify location (latitude and longitude) and calculate distance and directions to nearby hospitals and orthopedic surgeon offices. GPS coordinates are used to track activity such as distance and pace of daily walking.

The one or more sensors can also include an imaging device, such as an image sensor, e.g., camera. A user may take photographs and/or videos for a personal journal/diary. The camera may be any type of camera, such as a digital camera including self-contained optics. In other examples, the camera may have several components, such as lenses, other optics, and processing circuitry that may or may not be housed within a single housing.

The one or more sensors can also include sleep activity sensors. Motion sensors in the device 120 or attached to can be connected to software to track sleep and wake activity.

The one or more sensors can also include blood glucose sensors. Data from optical sensors glucose sensors attached to the device that record glucose concentration from blood or tears will be recorded and time-trended in the interactive guide.

The one or more sensors can also include body function sensors. Data from sensors in the device or attached to it will be used to record heart rate, heart rhythm, skin temperature, blood oxygen and carbon dioxide concentration, and blood alcohol level.

The one or more sensors can also include foot sensors. In this regard, data from sensors in socks or ankles will be used to record steps, speed, distance, cadence and foot-landing patterns in the interactive guide.

The one or more sensors can also include blood chemical sensors. In this regard, data from sensors can be used to detect chemical and hormones in saliva, blood or mucous will be recorded and time-trended in the interactive guide.

The one or more sensors can also include a compass. Data from the compass can be used to record knee range of motion.

The one or more sensors can also include a proximity sensor, ambient light sensor, and moisture sensor. These sensors, when attached to the device or accessed within it can be used to record usage activity, environment, and time trends.

The one or more sensors can also include sensors for detecting temperature, oxygen saturation, pulse, moisture, pain, location, motion, acceleration, device orientation for range of motion, etc.

The client device 120 may also include a display 128, such as an LCD, plasma, touch screen, or the like.

The client device 120 may include a mobile device, such as a mobile phone or a tablet computer owned and operated by a user (e.g., patient). The computing device 110 can be a server located on the premises of a health care facility, such as a hospital, clinic, etc. In another example, the server can be located offsite of the health care facility and can be connected to an internal health care network by one or more secure connections. In still another example, the server can be located off-site in a HIPAA compliant data storage facility and can be accessible to the patient and or the health care facility by a secure connection (after proper user authentication).

Figure 2:
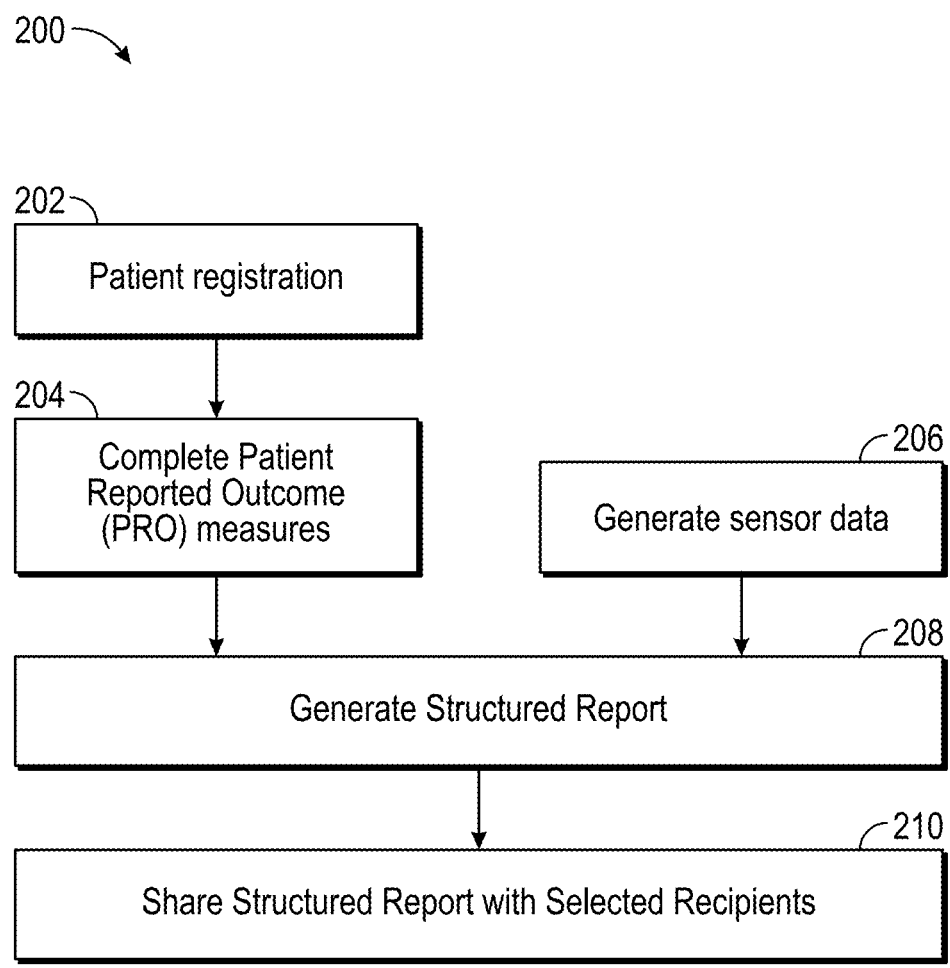
FIG. 2 is a flow chart depicting a method of interactive health care according to one or more aspects of the disclosure.
Figure 3:
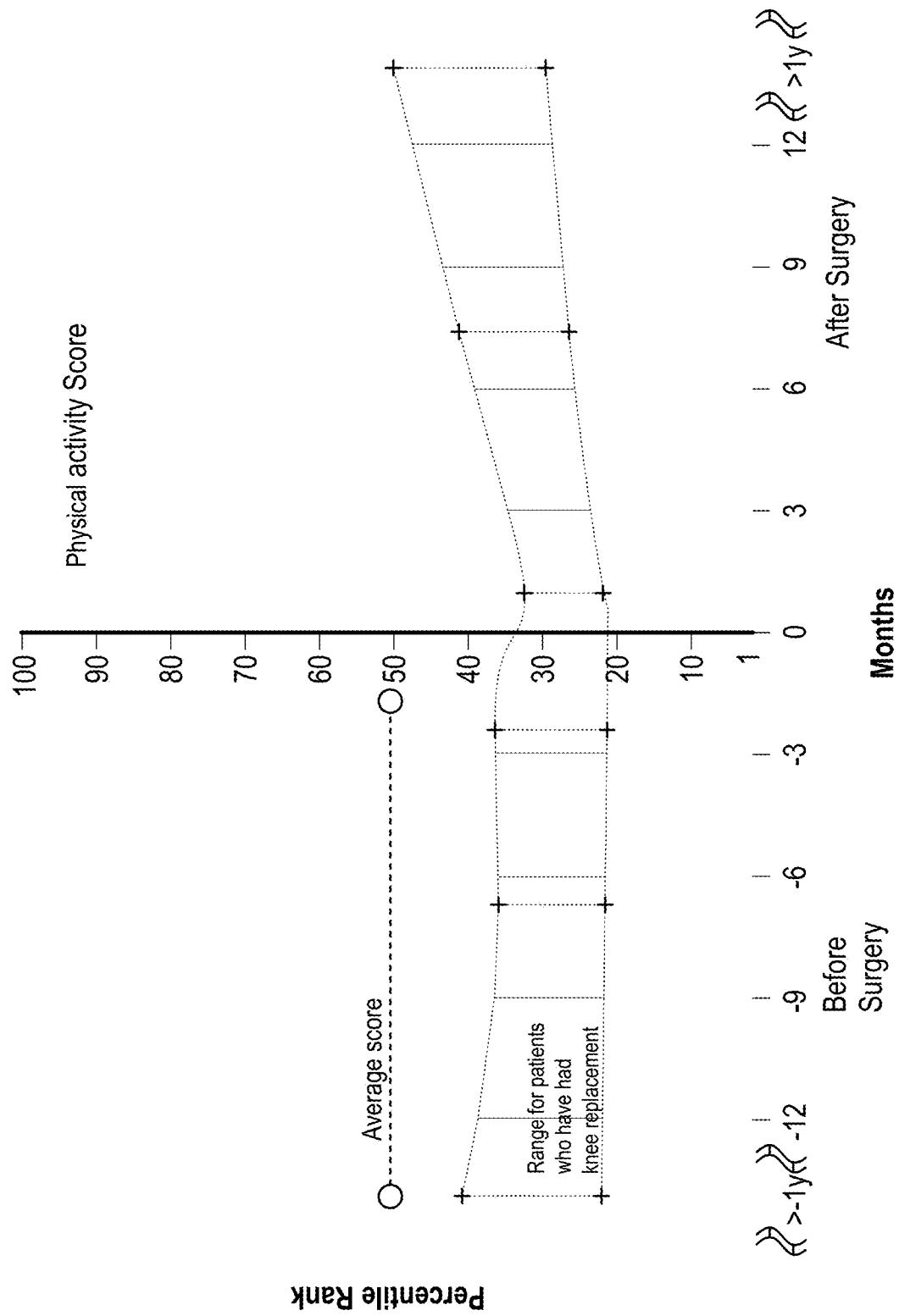
FIG. 3 is a chart depicting benchmarks for physical activity scores.

FIG. 2 depicts a flow chart 200 of developing a pain management regiment according to one or more aspects of the disclosure.

At block 202, the patient can register with the interactive health care system. This can be done by providing identifying information to the interactive health care system, such as: Name (identity authenticated); Date of birth (verified with ID); Address (verified with ID); Gender (verified with ID); Mobile number; and/or Email. The interactive health care system can authenticate the user with multi-factor authentication by providing a one-time code to a mobile phone number provided by the patient.

At block 204, the patient can complete one or more Patient Reported Outcome (PRO) measures. Exemplary questions that can form a portion of a PRO measure can be seen at FIG. 4. The PRO measures can include one or more medically-validated surveys, such as PROMIS CAT, DISABILITY, and/or NIH RTF MDS Back Pain and NIH RTF MDS Neck Pain, SOCIAL, and/or MEDICAL.

The PROMIS CAT (computer adapted test) can include up to 1600 questions that can be posed to the patient depending on answers to previous questions. For example, a patient's age can provide a starting group or sequence of questions that can be different for different age groups. One advantage of the PROMIS CAT is the ability to efficiently arrive at rankings and scores for individuals. Based on the adaptive techniques of the PROMIS CAT, the PROMIS CAT in some examples can include approximately 16 questions and takes an estimate 4 to 8 minutes for a patient to complete. The PROMIST CAT can include questions relating to physical function, pain interference, sleep disturbance, and/or depression symptoms. The interactive health care system can prompt the patient to complete the PROMIS CAT at predetermined times following a healthcare provider visit, such as 30 days, 90 days, 365 days, annually, etc.

The DISABILITY measure can be in the form of a human diagram and allow a patient to identify different parts of the body and provide pain and/or disability assessments for each, such as back pain, neck pain, back disability, and/or neck disability.

The NIH RESEARCH STANDARDS FOR CHRONIC BACK PAIN (NIH RTF MDS Back) and NECK PAIN (NIH RTF MDS Neck) can include up to 38 questions that relate to any number of risk factors for back or neck pain, including anxiety or depression.

The SOCIAL measure can include self-administered items from the NIH RTF MDS. The self-administered items can include a questionnaire regarding height, weight, tobacco use, alcohol over-use risk, employment status, education level, race, and/or ethnicity of the patient.

The MEDICAL measure can include self-administered Charlson Comorbidity Index.

Further questionnaires can include Back Pain Severity, Back Pain History, Back Pain Impact, Medical History, Shared Decision Making, and Safety Outcomes.

The Back Pain History questionnaire can includes questions relating to Pattern of Back Pain; Back Pain Duration; Back Pain Frequency; Lumbar Radicular Pain; Lumbar Radiculopathy; Back Surgery; Time since Back Surgery; Back Fusion; Back Injection; Time since Back Injection; Physical Therapy; Time since PT; Opioids; Current Opioids; CBT.

The Impact of Back Pain questionnaire can include questions relating to Time Off; Disability; Accident; Lawsuit; Fear Avoidance; Catastrophizing; Goal; Stomach pain (complex regional pain risk); Headaches (possible migraine risk); Pain in arms or legs (possible arthritis risk); Widespread pain (possible fibromyalgia risk).

The Medical History questionnaire can include questions relating to Heart attack; Heart failure; Vascular disease; Thrombosis; Bleeding; Stroke; Hemiplegia; Asthma; Asthma requiring medications; COPD; Dependence on oxygen; Peptic ulcer; Gastric ulcer; Diabetes; Diabetic retinopathy; Diabetic nephropathy; Chronic kidney disease; Dialysis; Cirrhosis; Transplant; Cancer; Mestastases; Leukemia; Lymphoma; HIV; Dementia; Inflammatory arthritis; Immunosuppressive medications; Osteoarthritis knees; Osteoarthritis hips.

The Shared Decision making questionnaire can includes questions relating to Knowledge gained by the patient; Treatment Preferences; and Integration of Preferences into Treatment Plans.

The Safety Outcomes questionnaire can includes questions relating to Opioids; Emergency Visit; Back Surgery; Back Injection; Physical Therapy; CBT; Time Off; Disability.

In contrast to certain prior art techniques, PRO measure responses and/or sensor data provided by the patient can stay with the patient no matter where the patient receives their care. This minimizes the risk of HIPAA noncompliance and avoids risk of confidentiality breaches.

At block 206, sensor data is received. This can be transmitted from computer 110 to computer 120 (either directly or indirectly) or can be provided directly to computer 110 by a user. The sensor data can include sensors used to assess back pain, such as measurement of temperature, oxygen saturation, pulse, moisture, pain, location, motion, acceleration, device orientation for range of motion, etc.

At block 208, the interactive health care system can generate a structured report based upon the PRO measures and/or the sensor data. The structured report can include one or more charts and/or benchmarked scores, including the following:

Physical Function chart and benchmarked scores (as shown in FIG. 5)
  Pain Interference chart and benchmarked scores (as shown in FIG. 5)
  Sleep Disturbance chart and benchmarked scores (as shown in FIG. 5)
  Depression Symptoms chart and benchmarked scores (as shown in FIG. 5)
  Back Pain Intensity chart
  Oswestry Back Disability chart
  Back Pain History Summary
  Neck Pain Intensity chart
  Neck Disability Index chart
  Neck Pain History Summary (as shown in FIG. 6)
  Social History Summary (as shown in FIG. 6)
  General Health Summary (as shown in FIG. 6)
  Problem List (as shown in FIG. 6)

As discussed above, the structured report can be shared with or provided to the patient upon completion of a measure, or at predetermined intervals. In one example, the intervals for reports and/or alerts can be 30 days, 60 days, 90 days, 3 months, 6 months, or annually as measured from a previous report, previous completion of a PRO measure, new sensor data, and/or a visit to a caregiver. In addition to alerts regarding new reports, the alerts can also include reminders or directives for the patient to take additional PRO measures, to engage in a form of therapy to improve overall condition (physical therapy, complete daily movement goals, take medication, etc.) The patient can receive the report at computer 120, which can include a software application ("app") that interfaces with server 110. That app can also include individualized prediction of outcomes as well as a dictionary of medical terms from trusted sources. Allowing the patient to view the structured report allows the patient to better understand their status relative to other patients with similar problems and allows the patient to better understand their progress and to be better informed in developing a pain management regiment with a care team.

The interactive health care system can integrate the PROMIS CAT-API for into graphical displays of longitudinal measurements. The PROMIS measurement system can use a T-score metric for reporting assessment scores. The PROMIS T-score can be normalized based on data from the US 2000 General Census, meaning that a PROMIS T-score of 50 is the mean with a standard deviation of 10. By standardizing the PROMIS measures on the same metric, interpretation across symptoms or functionality is simplified. All PROMIS measures can be centered on a T-score of 50 and any change of 5 to 10 points are considered meaningful.

The NIH Task Force on Research Standards for Chronic Low Back Pain patient survey includes screening questions for component conditions contributing to chronic low back pain. The present application can generate and transmit alerts that patients will be encouraged to discuss with their providers. To avoid confusion, mixed messages to patients, and duplication of effort by providers, the alerts can be transmitted to the patient. The alerts can include a set of evidence-based initial prescriptions for each condition that is targeted to the provider that would primarily manage this condition.

At block 210, the one or more structured reports can be transmitted, shared, or sent with selected recipients. This can be accomplished using the "app" on computer 120. The selected recipients can include one or more persons on the patient's care team, including doctor, nurse, physical therapist, etc. The selected recipients can also include the patient himself. Prior to transmission, the patient must consent for the use of unencrypted e-mails to be provided to the recipients to avoid unauthorized data access and/or to ensure HIPAA compliance. Once the report is received by a caregiver, the patient and the caregiver can engage in Shared Decision Making (SDM) in order to arrive at a care strategy specific to the patient.

Figure 7C:
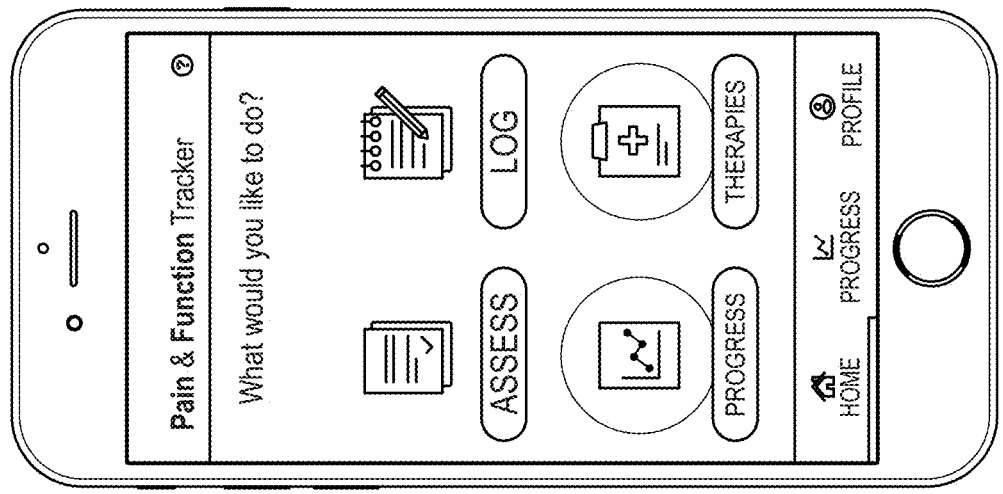
FIGS. 7A-7L depict various screens of a graphical user interface of an interactive health care system displayed on a mobile device
Figure 7B:
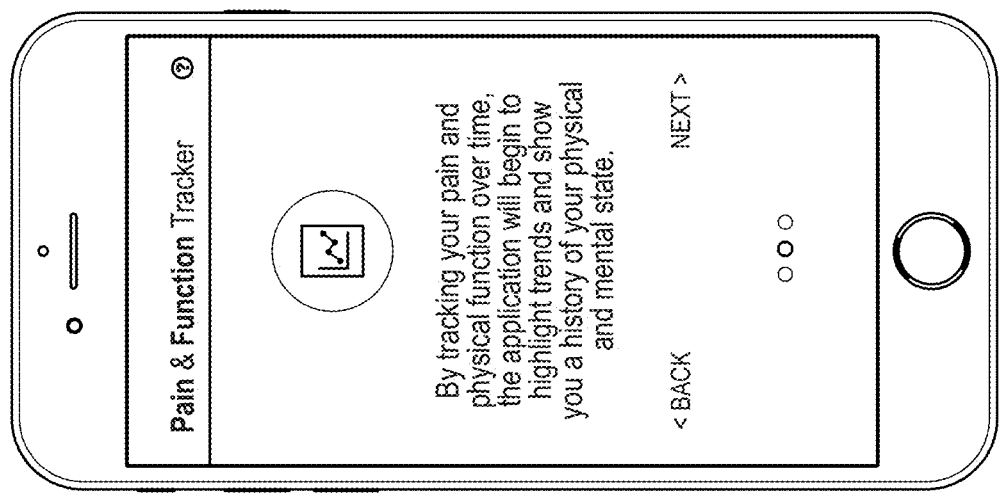
Figure 7A:
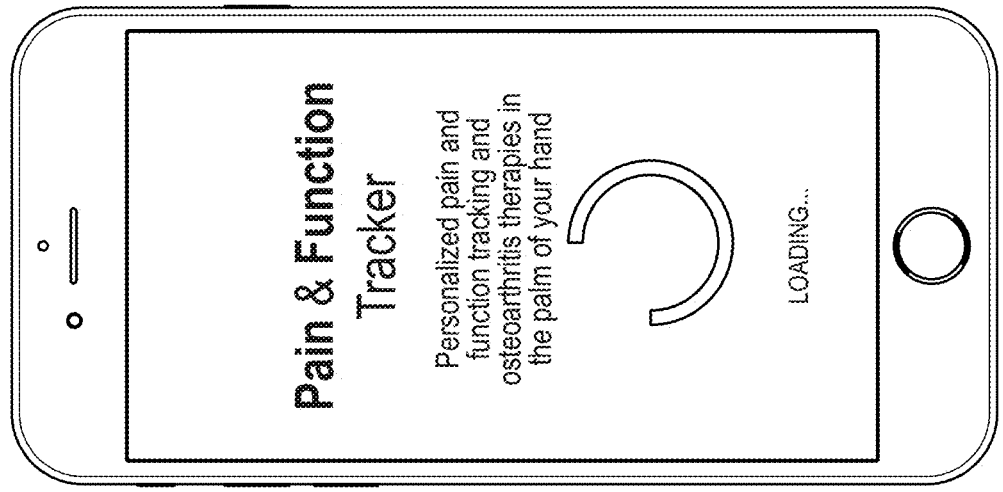
Figure 7F:
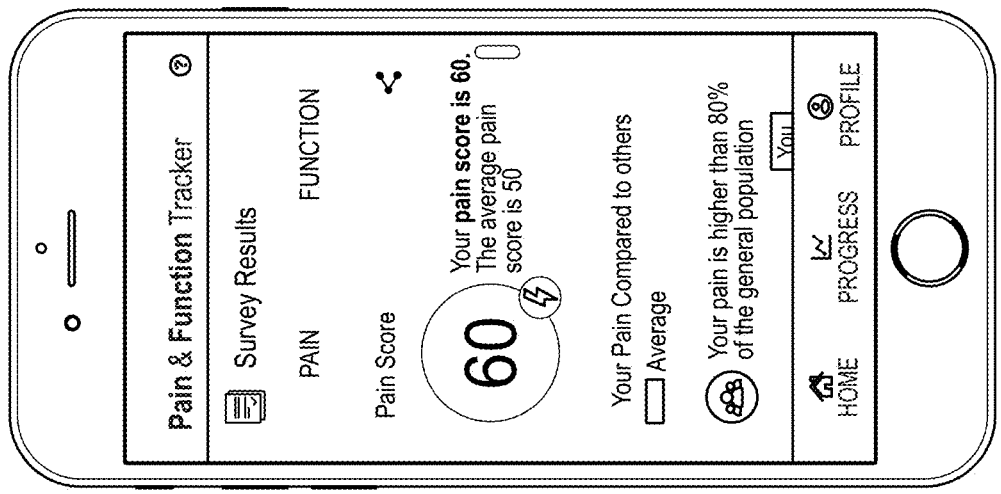
Figure 7E:
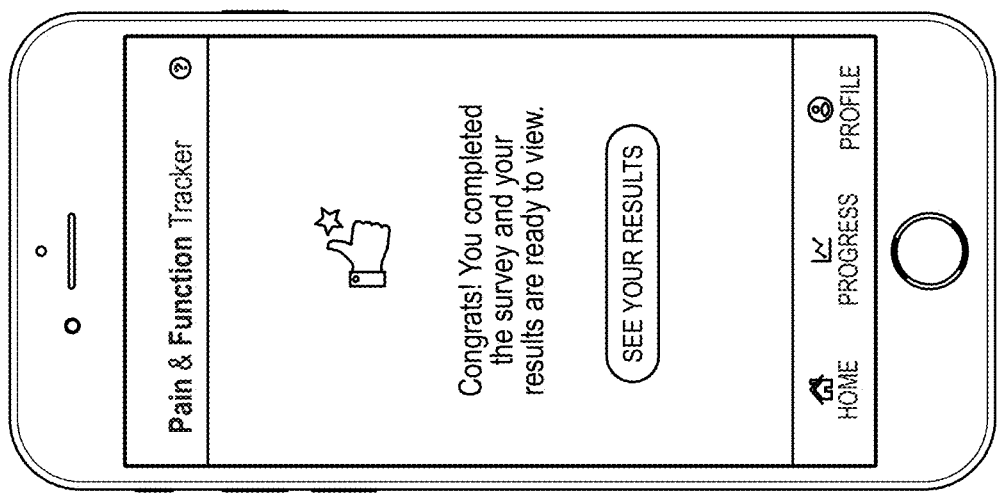
Figure 7D:
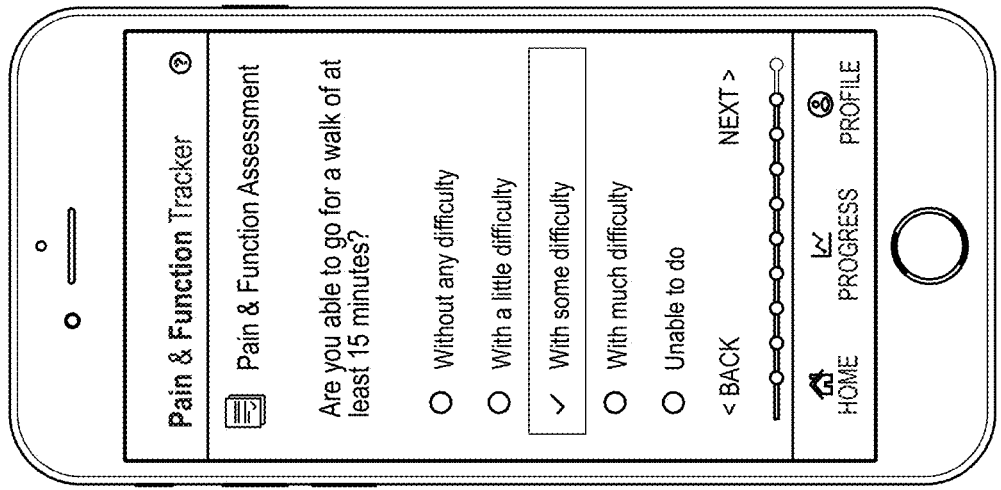
Figure 7I:
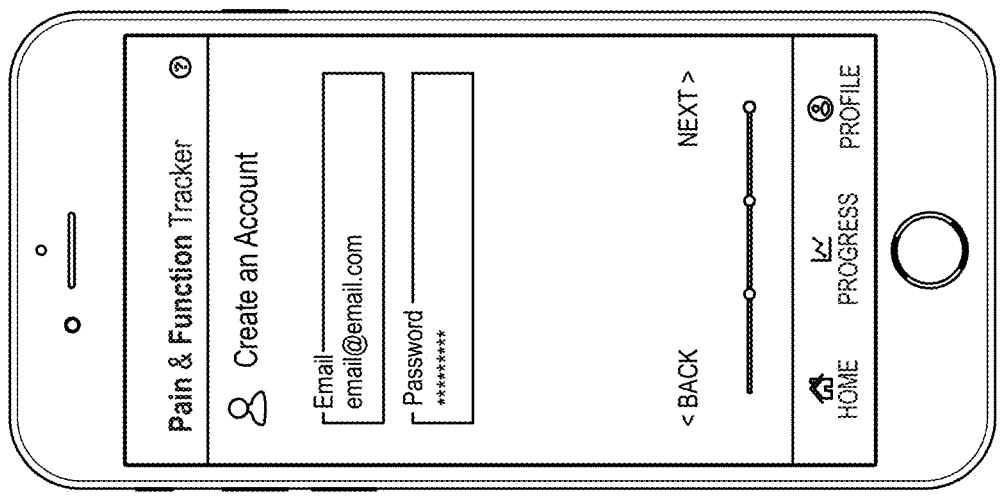
Figure 7H:
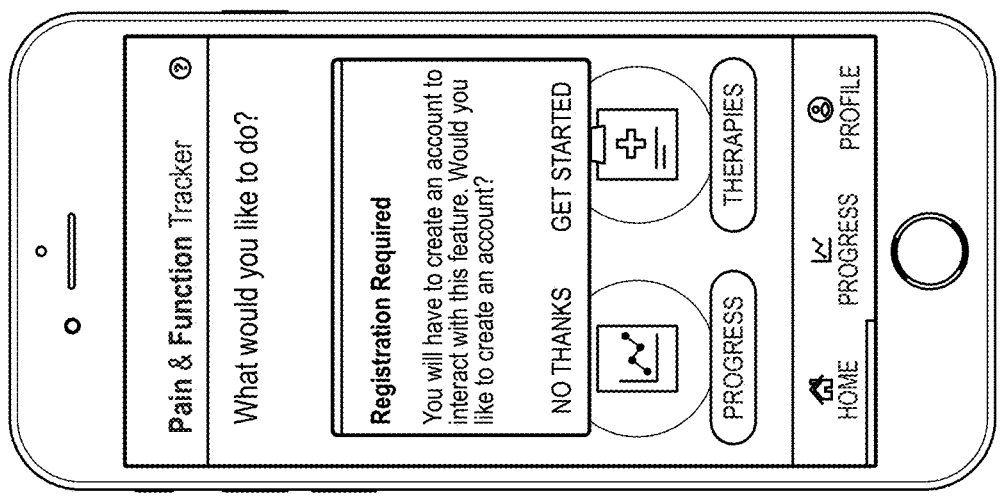
Figure 7G:
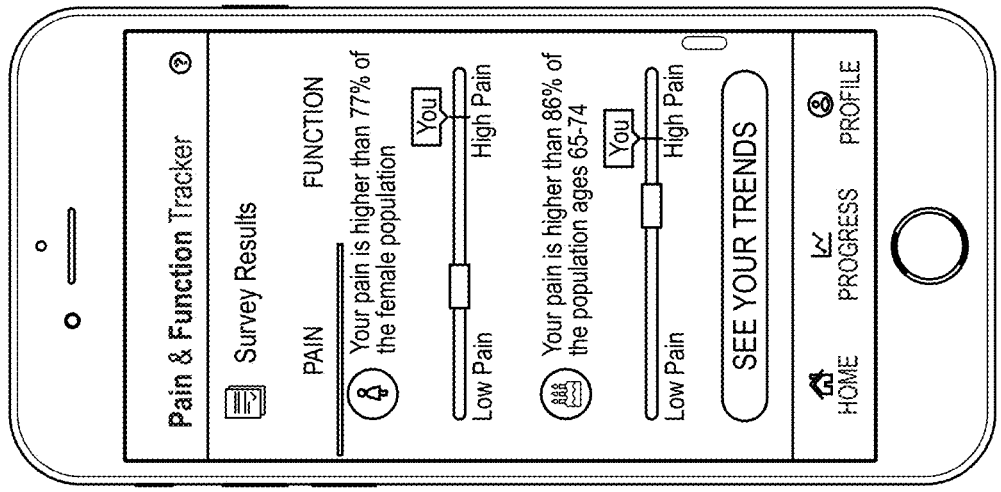
Figure 7L:
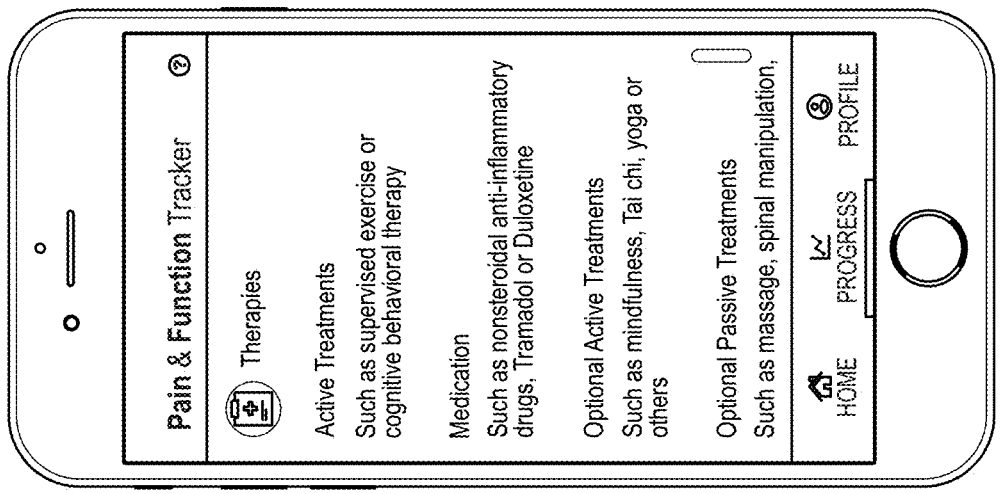
Figure 7K:
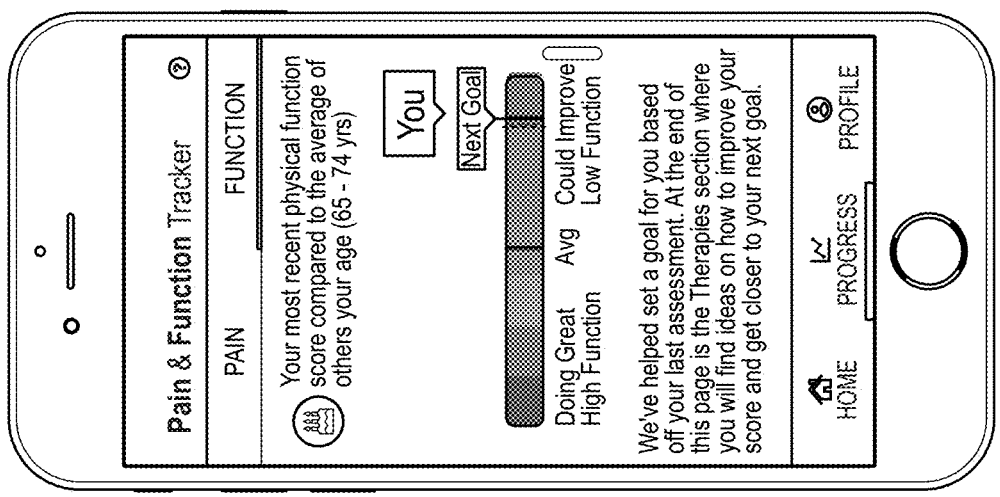
Figure 7J:
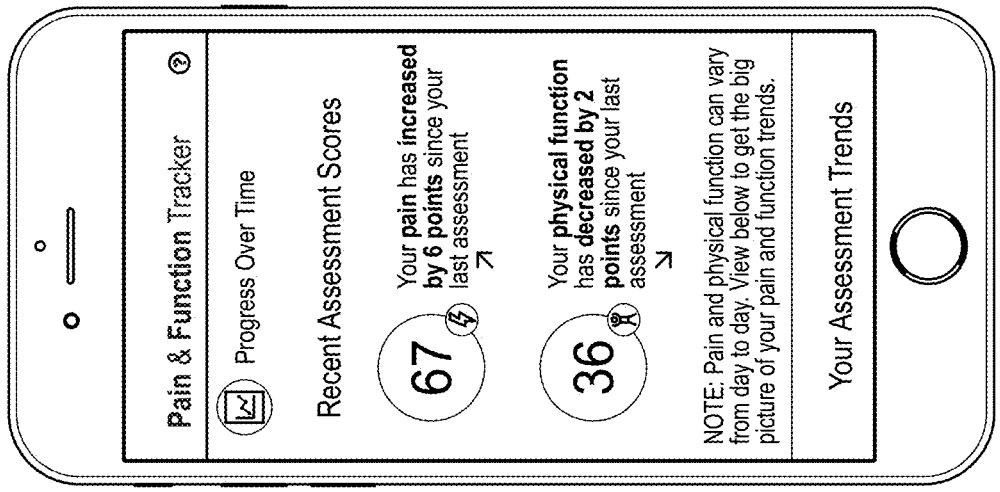

FIGS. 7A-7L depict various screens of a graphical user interface of an interactive health care system displayed on a mobile device. FIG. 7A depicts a home screen of the interactive health care system displayed on a mobile device. FIG. 7B depicts an introductory screen of the interactive health care system displayed on a mobile device. FIG. 7C depicts a selection screen of the interactive health care system displayed on a mobile device, with the options of viewing assessment, log, progress, and therapies options. FIG. 7D depicts an assessment screen of the interactive health care system displayed on a mobile device, with the user/patient being surveyed about walking ability. FIG. 7E is a screen indicating completion of a survey of the interactive health care system displayed on a mobile device. FIG. 7F is a survey result screen depicting a pain score and a comparison to general population of the interactive health care system displayed on a mobile device. FIG. 7G is a survey results screen depicting pain comparisons to gender population and age group of the interactive health care system displayed on a mobile device. FIG. 7H is a registration interface of the interactive health care system displayed on a mobile device. FIG. 7I is an account creation screen of the interactive health care system displayed on a mobile device. FIG. 7J is a progress over time screen showing recent assessment scores and progress since a previous assessment relative to pain and physical function of the interactive health care system displayed on a mobile device. FIG. 7K is a physical function screen showing recent physical function score compared to age group and a goal for future assessment of the interactive health care system displayed on a mobile device. FIG. 7L is a therapies screen showing treatments, medication, active treatments, and passive treatments of the interactive health care system displayed on a mobile device.

The interactive health care system incorporates one or more surveys, sensor data, and other health data received from the patient in order to help patients with Shared Decision Making (SDM) in conjunction with health care providers. With respect to privacy of shared data, the patient/user will be given notice of what information is being collected, the choice of what data to share, access to the collected data, security measures to protect the collected data, and redress if any data kept secure and private. Any data collected may be anonymized and added to a database to aid in future SDM of other patients, with personally identifiable information removed. In one example, this may be done only with the consent of the patient.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. Also, as used herein the terms "process" and/or "processor" should be taken broadly to include a variety of electronic hardware and/or software based functions and components (and can alternatively be termed functional "modules" or "elements"). Moreover, a depicted process or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Additionally, as used herein various directional and dispositional terms such as "vertical", "horizontal", "up", "down", "bottom", "top", "side", "front", "rear", "left", "right", and the like, are used only as relative conventions and not as absolute directions/dispositions with respect to a fixed coordinate space, such as the acting direction of gravity. Additionally, where the term "substantially" or "approximately" is employed with respect to a given measurement, value or characteristic, it refers to a quantity that is within a normal operating range to achieve desired results, but that includes some variability due to inherent inaccuracy and error within the allowed tolerances of the system (e.g. 1-5 percent). Accordingly, this description is meant to be taken only by way of example, and not to otherwise limit the scope of this invention.

What is claimed is:

1. A system for guiding a user through a shared decision making care plan including an initial diagnosis phase, a prognosis phase, a treatment phase, a rehabilitation phase, and a long-term care phase, wherein the phases of care are with respect to back and neck pain, comprising:
    a mobile device comprising:
        a touch screen interface for presenting sequences of survey questions to determine a Patient Reported Outcome measure in a plurality of the phases of shared decision making care plan, wherein at least one question of at least one of the sequences of survey questions is adaptive such that the question is selected based in part on a response to at least one previous question and the phase of shared decision making care plan, and wherein one or more of the survey questions are sourced from a PROMIS CAT database, and further wherein a plurality of the questions of the at least one of the sequences of survey questions comprise questions relating to physical function, pain interference, sleep disturbance, and depression symptoms, and further wherein the interface is further adapted to receive user input with respect to back or neck status, wherein the user input comprises responses to the survey questions, a plurality of sensors that measure at least one characteristic indicative of neck or back pain status, wherein the plurality of sensors comprises one or more accelerometers or gyroscopes, wherein the one or more accelerometers or gyroscopes measure user activity and mobile device orientation for tracking user motion and for modifying a display orientation and display contents of the interface, one or more Global Positioning System (GPS) sensors, wherein the GPS sensors track activity comprising distance and pace of walking, one or more imaging devices, one or more body function sensors for sensing body function data of a user, wherein the body function data comprises heart rate, heart rhythm, skin temperature, and blood oxygen and carbon dioxide concentration, one or more ambient light sensors, one or more sleep activity sensors comprising motion sensors, one or more blood glucose sensors comprising optical sensors for recording blood glucose concentration from one or more of blood or tears, one or more foot sensors, wherein the foot sensors record steps, speed, distance, cadence, and foot-landing patterns, one or more blood chemical sensors, wherein the blood chemical sensors detect one or more of chemicals and hormones in saliva, blood, and mucous, a compass, a proximity sensor, and one or more moisture sensors, and one or more data ports, wherein one or more of the ambient light sensors, motion sensors, optical glucose sensors, body function sensors, and proximity sensors are removably attached to the mobile device via the one or more of the data ports, a plurality of modules executing on one or more processors of at least one of the mobile device or a server that communicates with the mobile device, the plurality of modules including:

a comparison module that receives the user input and the at least one characteristic and compares the user input to benchmark medical data and validated medical sources, wherein the user input comprises responses to one or more survey questions, wherein the one or more survey questions are adaptive such that sequences of questions are selected based in part on a response to a least one previous question and the one or more survey questions are sourced from a PROMIS database, a usage activity recording module that receives information from the proximity sensor, an environment recording module that receives information from one or more of the ambient light sensors and one or more of the moisture sensors, a report module that provides a structured report to the user including personalized prediction of outcomes, a physical function goal, and therapies for achieving the goal, via the touch screen interface, based on the user input, the at least one characteristic, and the comparison, wherein the structured report further graphically depicts a plurality of Patient Reported Outcome measures compared with a plurality of corresponding age-differentiated and gender-differentiated benchmarked scores, wherein the report module further provides a prompt in the touch screen interface to the user to complete at least one of the sequences of survey questions from the PROMIS CAT database at a predetermined time following a healthcare provider visit for continuing the shared decision making care plan; and a server in communication with the mobile device and located at a HIPAA-compliant data storage facility for storing at least one of the user input or sensor data.

2. The system of claim 1, further comprising wherein the mobile device further comprises a registration module for registration registering a patient with the interactive health care system.

3. The system of claim 1, wherein the imaging device comprises a digital camera comprising component optics, wherein the digital camera and the component optics are not housed within a single housing.

4. A non-transitory computer readable medium containing program instructions for causing a computer to perform the method of guiding a user through a shared decision making care plan including an initial diagnosis phase, a prognosis phase, a treatment phase, a rehabilitation phase, and a long-term care phase, wherein the phases of care are providing a guide for practitioners with respect to back and neck pain, comprising:

presenting sequences of survey questions via an electronic interface to a user to determine a Patient Reported Outcome measure in a plurality of the phases of the shared decision making care plan, wherein at least one question of at least one of the sequences of survey questions is adaptive such that the question is selected based in part on a response to at least one previous question, and wherein one or more of the survey questions are sourced from a PROMIS CAT database, and further wherein a plurality of the questions of the at least one of the sequences of survey questions comprise questions relating to physical function, pain interference, sleep disturbance, and depression symptoms;

prompting the user to complete at least one of the sequences of survey questions from the PROMIS CAT database at a predetermined time following a healthcare provider visit by the user for continuing the shared decision making care plan;

receiving user input with respect to back or neck status, wherein the user input comprises responses to the survey questions;

measuring at least one characteristic indicative of neck or back pain status using a plurality of sensors, wherein the step of measuring comprises measuring motion, user activity, and orientation of a mobile device using one or more accelerometers or gyroscopes,
measuring activity comprising distance and pace of walking using one or more Global Positioning System (GPS) sensors,
recording one or more of images or video using one or more imaging devices,
measuring body function data of a user using one or more body function sensors, wherein the body function data comprises heart rate, heart rhythm, skin temperature, and blood oxygen and carbon dioxide concentration,
measuring sleep activity using one or more sleep activity sensors comprising motion sensors,
measuring blood glucose concentration from one or more of blood or tears using one or more blood glucose sensors comprising optical sensors,
measuring steps, speed, distance, cadence, and foot-landing patterns using one or more foot sensors located in at least one sock or on at least one ankle,
detecting one or more of chemicals or hormones in one or more of saliva, blood, or mucous using one or more blood chemical sensors,
measuring orientation using a compass,
measuring proximity using a proximity sensor, and
measuring moisture level using one or more moisture sensors;
recording the at least one characteristic indicative of neck or back pain status;
comparing the user input to benchmark medical data and validated medical sources;
calculating usage activity using information measured by the proximity sensor;
recording environment information received from one or more of the ambient light sensors and one or more of the moisture sensors;
providing a structured report to the user including personalized prediction of outcomes, a physical function goal, and therapies for achieving the goal, via a touch screen interface, based on the user input and the at least one characteristic and in response to the comparing step, wherein the structured report further graphically depicts a plurality of Patient Reported Outcome measures compared with a plurality of corresponding age-differentiated and gender-differentiated benchmarked scores; and
sending the user input and information from the measuring step to a server located at a HIPAA-compliant data storage facility.

5. A method for guiding a user through a shared decision making care plan including an initial diagnosis phase, a prognosis phase, a treatment phase, a rehabilitation phase, and a long-term care phase, wherein the phases of care are providing a guide for practitioners with respect to back and neck pain, comprising:
presenting sequences of survey questions via an electronic interface to a user to determine a Patient Reported Outcome measure in a plurality of the phases of the shared decision making care plan, wherein at least one question of at least one of the sequences of survey questions is adaptive such that the question is selected based in part on a response to at least one previous question and the phase of the shared decision making care plan, and wherein one or more of the survey questions are sourced from a PROMIS CAT database, and further wherein a plurality of the questions of the at least one of the sequences of survey questions comprise questions relating to physical function, pain interference, sleep disturbance, and depression symptoms;
prompting the user to complete at least one of the sequences of survey questions from the PROMIS CAT database at a predetermined time following a healthcare provider visit by the user for continuing the shared decision making care plan;
receiving user input with respect to back or neck status, wherein the user input comprises responses to the survey questions;
measuring at least one characteristic indicative of neck or back pain status using a plurality of sensors, wherein the step of measuring comprises
measuring motion, user activity, and orientation of a mobile device using one or more accelerometers or gyroscopes,
measuring activity comprising distance and pace of walking using one or more Global Positioning System (GPS) sensors,
recording one or more of images or video using one or more imaging devices, measuring body function data of a user using one or more body function sensors, wherein the body function data comprises heart rate, heart rhythm, skin temperature, and blood oxygen and carbon dioxide concentration,
measuring sleep activity using one or more sleep activity sensors comprising motion sensors,
measuring blood glucose concentration from one or more of blood or tears using one or more blood glucose sensors comprising optical sensors,
measuring steps, speed, distance, cadence, and foot-landing patterns using one or more foot sensors located in at least one sock or on at least one ankle,
detecting one or more of chemicals or hormones in one or more of saliva, blood, or mucous using one or more blood chemical sensors,
measuring orientation using a compass,
measuring proximity using a proximity sensor, and
measuring moisture level using one or more moisture sensors;
recording the at least one characteristic indicative of neck or back pain status;
comparing the user input to benchmark medical data and validated medical sources;
calculating usage activity using information measured by the proximity sensor;
recording environment information received from one or more of the ambient light sensors and one or more of the moisture sensors;
providing a structured report to the user including personalized prediction of outcomes, a physical function goal, and therapies for achieving the goal, via a touch screen interface, based on the user input and the at least one characteristic and in response to the comparing step, wherein the structured report further graphically depicts a plurality of Patient Reported Outcome measures compared with a plurality of corresponding age-differentiated and gender-differentiated benchmarked scores; and
sending the user input and information from the measuring step to a server located at a HIPAA-compliant data storage facility.

* * * * *